United States Patent [19]

Engel et al.

[11] Patent Number: 4,973,782

[45] Date of Patent: Nov. 27, 1990

[54] PREPARATION OF 2,2-DIETHYLTOLUENE

[75] Inventors: Dusan J. Engel, Des Plaines; Thomas P. Malloy, Lake Zurich, both of Ill.

[73] Assignee: UOP, Des Plaines, Ill.

[21] Appl. No.: 419,182

[22] Filed: Oct. 10, 1989

[51] Int. Cl.$^5$ ............................................... C07C 2/68
[52] U.S. Cl. .................................... 585/467; 585/468
[58] Field of Search ................................ 585/467, 468

[56] References Cited

FOREIGN PATENT DOCUMENTS 7018846  6/1970  Japan ................................. 585/467
62-138440  6/1987  Japan .
1014750  12/1965  United Kingdom ................ 585/468

OTHER PUBLICATIONS

Handbook of Petroleum Refining Processes, edited by Robert A. Meyers, 8-80, et ff., McGraw-Hill Book Company, (1986).

*Primary Examiner*—H. M. S. Sneed
*Assistant Examiner*—J. Saba
*Attorney, Agent, or Firm*—Thomas K. McBride; Eugene I. Snyder

[57] ABSTRACT

A diethyltoluene mixture rich in 2,5-diethyltoluene and containing less tha 5% of the 3,5-diethyltoluene can be prepared by methylating 1,4-diethylbenzene with an excess of methanol in the presence of amorphous silica-alumina catalysts. The most desirable catalysts have a silica:alumina ratio from about 2:1 through about 9:1. Methylation is conveniently effected in a temperature range between about 300° C. and about 450° C. and most desirably in a hydrogen atmosphere.

18 Claims, No Drawings

# PREPARATION OF 2,2-DIETHYLTOLUENE

BACKGROUND OF THE INVENTION

It has been observed that 2,5-diethyltoluene (2,5-DET) is an excellent desorbent in certain separations using a simulated moving bed, such as Sorbex TM separations technology (see, for example, Handbook of Petroleum Refining Processes, edited by Robert A. Meyers, 8–80 et ff., McGraw-Hill Book Company (1986)). Unfortunately, the material commonly available as 2,5-diethyltoluene is a mixture containing substantial proportions of the 3,5- and 2,6-isomer, and may also contain significant amounts of p-cymene (4-isopropyltoluene). The separation of such a mixture is itself difficult, so that relatively pure 2,5-diethyltoluene is not available in commercial quantities, and any separation performed to provide the latter would be prohibitively expensive. To compound the problems associated with the use of commercially available 2,5-DET, although some of the DET isomers are "neutral", in the sense of neither hindering nor promoting the adsorbent properties of the 2,5-isomer, other isomers, such as 3,5-diethyltoluene, are definitely deleterious and desirably should be present in as low a level as possible when 2,5-diethyltoluene is used as a desorbent.

Although the methylation of 1,4-diethylbenzene would appear to be the logical choice of means for preparing 2,5-diethyltoluene, such a method is rife with difficulties, some foreseen, others unanticipated. A catalyst which promotes alkylation also promotes the migration of alkyl groups on the ring (i.e., intramolecular alkylation), so that the production of isomers where the ethyl groups are not in the para-orientation may be anticipated. A catalyst which promotes alkylation also promotes transalkylation (i.e., intermolecular alkylation) where the ethyl group from one molecule is transferred to another molecule giving one monoethylbenzene molecule and one triethylbenzene molecule. A catalyst which promotes alkylation also promotes dealkylation, i.e., removal of alkyl groups from the ring, thereby affording monoethylbenzene. Finally, catalysts which promote alkylation are generally nonspecific, affording a range of mono- and polyalkylated products.

In view of the foregoing remarks the task of preparing 2,5-diethyltoluene containing a limited and well defined isomer distribution and with minimal polyalkylation and dealkylation products seemed formidable indeed. Consequently we were delighted and rather surprised to find that certain catalysts appeared to effect the methylation of 1,4-diethylbenzene with the desired selectivity. More particularly, when methanol was the alkylating agent in at least, and preferably more than, one molar proportion relative to 1,4-diethylbenzene it was found that quite good selectivity was achieved, rather contrary to the expectation that optimum selectivity would occur at a methanol concentration equivalent to less than one molar proportion.

SUMMARY OF THE INVENTION

The purpose of this invention is to prepare 2,5-diethyltoluene. More particularly, the purpose is to prepare 2,5-diethyltoluene in a DET mixture at least 80% of which consists of the 2,5- and 2,6-isomers and which contains less than 5% of 3,5-diethyltoluene. An embodiment comprises reacting 1,4-diethylbenzene (p-diethylbenzene, or p-DEB) with more than one molar proportion methanol in the presence of an amorphous silica-alumina catalyst. In a more specific embodiment the catalyst contains a silica to alumina ratio between 1:3 and 9:1. In another specific embodiment the methanol is present in from 1.5 to 2.5 molar proportions. In yet another embodiment the reaction is conducted in the presence of hydrogen. Still other embodiments will be apparent from the ensuing discussion.

DESCRIPTION OF THE INVENTION

The feedstock which is methylated is 1,4-diethylbenzene. Normally the feedstock which is used is at least 98% pure, although this is not a critical feature of our invention. The 1,4-diethylbenzene is usually used per se, i.e., no solvent is used in the reaction. Generally the use of a solvent is not only unnecessary but also undesirable in the sense of diluting both reactant and product, with the requirement of solvent separation from the product being an additional process cost. However, where other considerations indicate a solvent, a suitable solvent may be used so long as it is unreactive under the reaction conditions and does not otherwise interfere either with the reaction or the mechanics of the reactor.

1,4-Diethylbenzene is methylated with methanol as the methylating agent. Since a mono-methylated product is desired, it might be thought that a molar excess of the diethylbenzene relative to methanol would be desirable. However, contrary to such expectations it has been found that from one to about three molar proportions of methanol are best in carrying out this reaction, with from about 1.5 to about 2.5 molar proportions methanol based on 1,4-diethylbenzene being preferred.

The p-DEB and methanol are then reacted in the presence of an alkylation catalyst, with amorphous silica-alumina being the preferred catalyst. The silica:alumina ratio in such catalysts may be from about 1:3 up to about 9:1, although acidic catalysts with the ratio from 2:1 through 9:1 are preferred. It appears that the most desirable silica-alumina is one with a silica:alumina ratio between about 2:1 and about 4:1.

Whereas amorphous silica-aluminas are the catalysts of choice, other catalysts also may be used in the practice of this invention and include HY zeolite (Y zeolite in the acid form) and mordenite. As previously stated, these latter catalysts do not appear to be as efficacious as amorphous silica-aluminas and are less favored in the practice of our invention.

The preparation of the diethyltoluenes according to our invention is preferably conducted in a continuous fashion, which requires a fixed mass of catalyst. However, the preparation also may be carried out in a batchwise manner, and when a batch mode is used the catalyst concentration is such that the weight ratio of methanol to catalyst is from about 2:1 to about 10.1.

The methylation of 1,4-diethylbenzene is conducted within the broad range of 300° to 450° C., with the range between 350° and 400° C. being favored. In a highly preferred optional embodiment the reaction is conducted in a hydrogen atmosphere at a pressure between about 500 to about 1500 psig with a recommended range between about 800 and about 1200 psig. When the reaction is conducted in the presence of hydrogen coke formation is somewhat diminished. Although coke formation has an adverse effect on reaction rate, or conversion at constant conditions, it has a beneficial effect on selectivity. Stated differently, coke formation decreases catalyst activity but increases catalyst selectivity. When coke formation is retarded, as it is in a hydrogen atmosphere, the resultant conversion/selectivity characteristics appear to be optimized.

As previously stated, the reaction can be effected either as a batch reaction or in a continuous mode, with the latter being the preferred mode of reaction. In this mode, a mixture of p-DEB and methanol containing from one to three molar proportions of methanol based on the diethylbezene is introduced into the reaction zone of a reactor. The reaction zone also contains a fixed mass of catalyst, generally as a fixed bed although an ebullating bed, radial bed, fluidized bed, and so forth, also can be used in the practice of our invention. The catalyst is preferably an amorphous silica-alumina where the silica:alumina ratio is from 1:3 to about 9:1, more usually from 2:1 up to about 9:1, with the range between about 2:1 to about 4:1 being particularly recommended. The reaction zone typically will be held at a temperature between about 300° and 450° C., but more usually between about 350° and 400° C. Priority is given to the reaction being conducted in the presence of hydrogen at a pressure between about 800 and about 1200 psig. Effluent is collected as the reaction product, and of the diethyltoluenes present at least 80% consist of the 2,5- and 2,6-diethyltoluene isomers. Just as importantly, there is no more than about 5% of the 3,5-diethyltoluene isomer, whose presence is found to be deleterious when the diethyltoluene mixture is used as the desorbent in various adsorption processes.

An important variant consists in separating the diethyltoluenes from the unreacted diethylbenzene in the effluent and returning the unreacted diethylbenzene to the reaction zone. In this way unreacted diethylbenzene can be continually recycled, ultimately leading to substantially higher conversions of diethylbenzene than are possible using a single pass.

The ensuring examples will disclose other embodiments and variants, all of which are intended to be encompassed within our invention. These examples are solely for the purpose of illustrating our invention and do not limit it in any way.

EXAMPLE I

Catalyst Screening

The methylation of 1,4-diethylbenzene by methanol was screened in a 300 cc stainless steel rocking autoclave outfitted with a glass liner. The catalyst, ratio of methanol to p-DEB, and reaction conditions as well as overall results, are summarized in the following table. All reactions were conducted for 8 hours, after which the reaction mixture was cooled, catalyst was separated, and liquid was analyzed by gas chromatography for p-DEB and DET's.

TABLE 1

Methylation of 1,4-diethylbenzene[a]

| Experiment No. | Catalyst | Molar Ratio CH₃OH/P-DEB | T °C. | Hydrogen, psig | % Conversion | % Selectivity DET[b] |
|---|---|---|---|---|---|---|
| 1 | HY | 1.5 | 250 | 1,000 | 5.7 | 85[c] |
| 2 | HY | 1.5 | 350 | 1,000 | 51.9 | 36[c] |
| 3 | mordenite | 1.5 | 350 | 1,000 | 16.6 | 49[d] |
| 4 | amorphous silica-alumina, 3:1 silica:alumina | 1.5 | 350 | 1,000 | 34.1 | 52[d] |
| 5 | amorphous silica-alumina, 3:1 silica:alumina | 0.5 | 280 | 1,000 | 5.4 | 75[d] |
| 6 | amorphous silica-alumina, 3:1 silica:alumina | 0.5 | 350 | 1,000 | 31.5 | 50[e] |
| 7[f] | amorphous silica-alumina, 3:1 silica:alumina | 0.5 | 350 | 1,000 | 28.7 | 43[e] |
| 8 | XN1010[g] | 1.5 | 180 | 200 | <5 | 0 |

[a]Weight ratio CH₃OH/catalyst = 3.2.
[b]Selectivity = (% DET formed/% DEB reacted) × 100.
[c]Minor amount (≦20%) 2,5-DET.
[d]Predominantly (≧70%) 2,5-DET.
[e]Some dealkylation to ethylbenzene
[f]Weight ratio CH₃OH/catalyst = 6.4.
[g]Strongly acidic ion exchange resin from Dow Chemical.

The foregoing table shows that even though HY was a moderately effective catalyst in producing diethyltoluenes from p-DEB, the desired 2,5-DET is formed only in minor amounts. Although the selectivity using an acid washed crystalline mordenite was relatively good, conversions remained low. The strongly acidic (sulfonic acid groups) ion exchange material used as a catalyst also failed to afford the desired diethyltoluenes. Even if the conversions observed with the amorphous silica-alumina were not outstanding, selectivity was quite acceptable. The amorphous silica-aluminas also are advantageous as a catalyst because of their resistance to water which is formed during the course of the reaction.

EXAMPLE II

Continuous Methylation of p-DEB

Continuous methylation of p-DEB was performed in a reactor of 7/8 inch bore having a reaction zone containing 40 cc (33.5 gram) of an amorphous silica (silica:alumina=3:1). The feedstock was a mixture of methanol and p-DEB at a ratio of 2:1 which was passed downflow over the catalyst bed at a liquid hourly space velocity of about 2. The effluent was analyzed by gas liquid chromatography for the amount of p-DEB reacted and the total amount of diethyltoluenes formed. The data are summarized in the following table.

TABLE 2

| | Continuous Methylation of p-DEB | | |
|---|---|---|---|
| Stream Hours | T °C. | Conversion % | Selectivity to DET % |
| 8 | 350 | 27.0 | 62 |
| 16 | " | 22.0 | 65 |
| 28 | " | 13.7 | 75 |
| 32 | " | 12.7 | 79 |
| 36 | 400 | 18.9 | 72 |
| 44 | " | 13.1 | 70 |
| 52 | " | 11.2 | 70 |

The catalyst seemed to deactivate rather quickly through coke formation, which was accompanied by a corresponding increase in selectivity. Effluent from 8 through 52 stream hours was collected and fractionated, and a cut of boiling point 198°-210° C. was analyzed by gas liquid chromatography for the isomeric diethyltoluenes and p-DEB with the following results: 2,5-DET, 74%; 2,6-DET, 12%; 2,3-DET+2,4-DET, 4%; 3,5-DET, 2%; p-DEB, 3%; others, 5%. As a base for comparison "polyethyltoluene" (obtained from Dow Chemical Co.) was fractionated to afford cuts containing from 3–44% 2,5-DET. That fraction containing the highest amount (44.3%) of the 2,5-isomer also contained 9.6% of the undesirable and deleterious 3,5-isomer, and other fractions contained as much as 41% of 3,5-DET. What this shows is both the difficulty of separating the isomeric DET's by fractionation, and the fact that commercial material contains an unacceptably high proportion of 3,5-DET..

What is claimed is:

1. A continuous method of making diethyltoluene, at least 80% of which consists of 2,5-diethyltoluene and 2,6-diethyltoluene isomers and which contains less than 5% of the 3,5-diethyltoluene isomer, comprising reacting one molar proportion of 1,4-diethylbenzene with from about 1.0 to about 3.0 molar proportions of methanol at a temperature from about 300° to about 450° C. in the presence of a fixed mass of a catalyst selected from the group consisting of amorphous silica-aluminas, where the silica:alumina ratio is between about 1:3 to about 9:1, and mordenite, or any combination thereof, and collecting the reaction product.

2. The method of claim 1 wherein the 1,4-diethylbenzene is reacted with from about 1.5 to about 2.5 molar proportions of methanol.

3. The method of claim 1 where the temperature is from about 350° to about 400° C.

4. The method of claim 1 further characterized in that the reaction is performed in a hydrogen atmosphere where the pressure of the hydrogen is from about 500 to about 1500 psig.

5. The method of claim 1 where the catalyst is an amorphous silica-alumina whose silica:alumina ratio is from about 2:1 to about 9:1.

6. The method of claim 5 where the catalyst has a silica:alumina ratio from about 2:1 to about 4:1.

7. A continuous method of making diethyltoluene, at least 80% of which consists of the 2,5-diethyltoluene and 2,6-diethyltoluene isomers, and which contains less than about 5% of the 3,5-diethyltoluene isomer comprising reacting in a reaction zone one molar proportion of 1,4-diethylbenzene with from about 1.0 to about 3.0 molar proportions of methanol at a temperature from about 300° C. to about 450° C. in the presence of a fixed mass of a catalyst selected from the group consisting of amorphous silica-aluminas, where the silica:alumina ratio is between about 1:3 to about 9:1, and mordenite, or any combination thereof, and collecting the reaction product, separating unreacted 1,4-diethylbenzene from the reaction product and recycling the 1,4-diethylbenzene to the reaction zone.

8. The method of claim 7 where the diethylbenzene is reacted with from about 1.5 to about 2.5 molar proportions of methanol.

9. The method of claim 7 where the temperature is from about 350° to about 400° C.

10. The method of claim 7 further characterized in that the reaction is performed in a hydrogen atmosphere where the pressure of the hydrogen is from about 500 to about 1500 psig.

11. The method of claim 7 where the catalyst is an amorphous silica-alumina whose silica:alumina ratio is from about 2:1 to about 9:1.

12. The method of claim 11 where the catalyst has a silica:alumina ratio from about 2:1 to about 4:1.

13. A method of making diethyltoluene, at least 80% of which consists of 2,5-diethyltoluene and 2,6-diethyltoluene isomers and which contains less than 5% of the 3,5-diethyltoluene isomer, comprising reacting one molar proportion of 1,4-diethylbenzene with from about 1.0 to about 3.0 molar proportions of methanol at a temperature from about 300° to about 450° C. in the presence of a catalyst selected from the group consisting of amorphous silica-aluminas, where the silica:alumina ratio is between 1:3 to about 9:1, and mordenite, or any combination thereof, where the weight ratio of methanol to said catalyst is between 2 and about 10, or any combination thereof, and collecting the reaction product.

14. The method of claim 13 where the 1,4-diethylbenzene is reacted with from about 1.5 to about 2.5 molar proportions of methanol.

15. The method of claim 13 where the temperature is from about 350° to about 400° C.

16. The method of claim 13 further characterized in that the reaction is performed in a hydrogen atmosphere where the pressure of the hydrogen is from about 500 to about 1500 psig.

17. The method of claim 13 where the catalyst is an amorphous silica-alumina whose silica:alumina ratio is from about 2:1 to about 9:1.

18. The method of claim 17 where the catalyst has a silica:alumina ratio from about 2:1 to about 4:1

* * * * *